United States Patent [19]

Cram et al.

[11] Patent Number: 4,474,699
[45] Date of Patent: Oct. 2, 1984

[54] PREPARING 1-AMINOMETHYL-6-SUBSTITUTED-4H-S-TRIAZOLO[4,3-A][1,4]BENZODIAZEPINES IN IMPROVED PROCEDURES

[75] Inventors: Donald J. Cram, Los Angeles, Calif.; Martin Gall; Michael F. Lipton, both of Kalamazoo, Mich.

[73] Assignee: The Upjohn Company, Kalamazoo, Mich.

[21] Appl. No.: 497,784

[22] Filed: May 25, 1983

[51] Int. Cl.$^3$ ............................................. C07D 487/04
[52] U.S. Cl. .............................. 260/245.5; 260/244.4
[58] Field of Search .......................... 260/244.4, 245.5

[56] References Cited

U.S. PATENT DOCUMENTS 3,987,052 10/1976 Hester, Jr. .................... 260/308 R
4,001,262 1/1977 Gall ................................. 260/296 T
4,250,094 2/1981 Hester, Jr. ...................... 260/245.5

OTHER PUBLICATIONS

Hester, J. Org. Chem., vol. 44, pp. 4165–4169, (1979).
Chem. Pharm. Bull., (Japan), 28, (8), 2536–2540, (1980), N. Inotsume, et al., "Reversible . . . Temperature".

Primary Examiner—Alton D. Rollins
Attorney, Agent, or Firm—John T. Reynolds

[57] ABSTRACT

An improved process for preparing a 1-aminomethyl-6-substituted-4H-s-triazolo[4,3-a][1,4]benzodiazepine product, e.g., adinazolam, directly from the corresponding 1-hydrogen-6-substituted-4H-s-triazolo[4,3-a][1,4]benzodiazepine starting material, e.g., from estazolam, by conducting the reaction between the estazolam-type compound and the dimethylaminomethylene salt in the selected solvent in the presence of an alkali metal carbonate, and thereafter extracting the 1-aminomethyl-6-substituted-4H-s-triazolo[4,3-a]-[1,4]benzodiazepine from an aqueous organic solvent mixture thereof into a halogenated $C_1$ to $C_3$-alkane solvent while maintaining the pH of the aqueous phase between pH 3.0 and 4.0, and thereafter recovering the product from the halogenated alkane solvent.

5 Claims, No Drawings

PREPARING 1-AMINOMETHYL-6-SUBSTITUTED-4H-S-TRIAZOLO[4,3-A][1,4]BENZODIAZEPINES IN IMPROVED PROCEDURES

INTRODUCTION

This invention relates to processes for preparing 1-aminomethyl-6-substituted-4H-s-triazolo[4,3-a][1,4]benzodiazepines. More particularly this invention provides an improved process for directly preparing 1-[(dimethylamino)methyl]-6-substituted 4H-s-triazolo[4,3-a][1,4]benzodiazepines (V) directly from the 1-unsubstituted-6-substituted-4H-s-triazolo[4,3-a][1,4]benzodiazepines (I) and the reagent

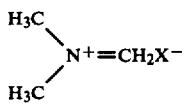

wherein X is the anion of an organic or inorganic acid.

BACKGROUND OF THE INVENTION

Gall, U.S. Pat. No. 4,001,262 describes and claims a process for reacting a 1-hydrogen-6-substituted-4H-s-triazolo[4,3-a][1,4]benzodiazepine with a reagent

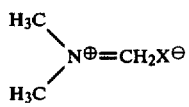

where $X^{\ominus}$ is the anion of a monovalent inorganic or organic acid, in solution such as in dimethylformamide, at 50° to 100° C. to form a 1-[(dimethylamino)methyl]-6-substituted-4H-s-triazolo[4,3-a][1,4]benzodiazepine. A specific application of that process would be to react 8-chloro-1-hydrogen-6-phenyl-4-H-s-triazolo[4,3-a][1,4]benzodiazepine (now known by the generic name estazolam) with dimethylaminomethylene chloride salt to form 8-chloro-1-[(dimethylamino)methyl]-6-phenyl-4H-s-triazolo[4,3-a][1,4]benzodiazepine (now known by the generic name, adinazolam). Estazolam and related compounds are described and claimed in Hester, Jr., U.S. Pat. No. 3,987,052, and in foreign equivalent patents of Takeda Chemical Company of Japan. Adinazolam is described and claimed with other compounds in Hester, Jr., U.S. Pat. No. 4,250,094. Additional 1-aminomethyl-6-substituted-4H-s-triazolo[4,3-a][1,4]benzodiazepine compounds, which can be made according to the improved process of this invention are described in the above Gall, U.S. Pat. No. 4,001,262, Hester, Jr., U.S. Pat. No. 3,734,922 and other patents and publications.

The process in the above Gall, U.S. Pat. No. 4,001,262 describes the need for chromatography procedures to separate and purify the desired 1-aminomethyl compound thereof (II) from the undesired but often coformed isomeric 4-aminomethyl- and 1,4-bis-aminomethyl-compounds as well as from by-product salts of the reaction. While column chromatography is convenient to use for purifying and separating chemical compounds on a laboratory scale, it is inconvenient for the purification of products in pilot plant or production plant scale procedures, where quantities of desired drug compounds are prepared on scales ranging from 5 to 5,000 kilograms per lot and larger. Moreover, silica gel, used for column chromatography, is costly, and such chromatography, if carried out at all, is time consuming and labor intensive.

Moreover, since the time of the invention described in the Gall, U.S. Pat. No. 4,001,262 chemical studies have continued by persons in the art to find practical methods for improving the yields of the desired 1-aminomethyl-product, e.g., adinazolam, over the whole course of this process including what goes on in the initial reaction mixture and in the subsequent work-up procedures. There is a need to improve the above referenced process for use in manufacturing 1-aminomethyl-compounds of the above Gall patent type, U.S. Pat. No. 4,001,262, which are of significant commercial and practical value as important and useful active drug compounds.

In studies of reactions of this process on related compounds attempts to minimize 4-aminomethyl- and 1,4-bis(aminomethyl)-group substitution in the ring system I, by inclusion of calcium hydride and 1,8-bis(dimethylamino)naphthalene have failed to minimize the formation of complicating side, by-product yield lowering 4-aminomethyl- and 1,4-bis(aminomethyl)-compounds.

The inventive advance in the art of carrying out the reaction and in identifying selective extractive conditions for separating the desired products (V), e.g., adinazolam, from their reaction mixture, solvents and by-products and the success of the resulting invention is reflected in the objects and description of the process improvements which follow.

OBJECTS OF THE INVENTION

It is an object of this invention to provide an improved, practical process for preparing valuable and useful 1-aminomethyl-6-substituted-4H-s-triazolo[4,3-a][1,4]benzodiazepines, which minimize formation of undesired by-products, and which is more efficient in separating the desired 1-aminomethyl-6-substituted-4H-s-triazolo[4,3-a][1,4]benzodiazepine product from its reaction, by-product salts and solvent system, without the need for column chromatography procedures.

In a particular application, this invention provides an improved process for directly converting estazolam to adinazolam in improved yields, without the need for column chromatography procedures.

Other objects, advantages and aspects of the invention will be apparent from the remaining specification and the claims which follow.

SUMMARY OF THE INVENTION

Briefly, we have discovered that the conversion of estazolam type compounds (I) to possible 4-aminomethyl-(III) and 1,4-bis(aminomethyl)-by-product-6-substituted-4H-s-triazolo[4,3-a][1,4]benzodiazepines (IV) can be minimized substantially and effectively by including in the estazolam/dimethylaminomethylene salt/DMF reaction mixture an alkali metal carbonate, preferably potassium carbonate, and then heating the mixture at about 20° to 60° C., preferably 47° to 60°, for about 2.5 to 16 hours to effect formation of the desired 1-aminomethyl-6-substituted-4H-s-triazolo[4,3-a][1,4]benzodiazepine product (V), e.g., adinazolam. We have also found that the desired 1-(aminomethyl)-6-substituted-4H-s-triazolo[4,3-a][1,4]benzodiazepine product (V) can be selectively extracted into a chlorinated hydrocarbon liquid solvent, e.g., methylene chloride, from an aqueous pH 3.0 to 4.0 solution, which procedure avoids the need for column chromatography purification procedures.

DETAILED DESCRIPTION OF THE INVENTION

In the accompanying chemical formulae sheet structures, $R_2$ in structure I, III, IV and V is hydrogen or a halogen having an atomic number of from 9 to 35, that is, fluorine, chlorine or bromine, or $R_2$ is trifluoromethyl or nitro, but $R_2$ is preferably chlorine or bromine, Y is trivalent nitrogen or the group $-CR_1=$, where $R_1$ is hydrogen, chloro or fluoro.

In formula II, $X^-$ is the anion of a monovalent organic or inorganic acid, preferably the anions of hydrochloric, hydrobromic, hydroiodic, trifluoroacetic, methanesulfonic, p-toluenesulfonic, and the like.

The formula I compounds are the starting materials for the process of this invention. They are referred to in Gall, U.S. Pat. No. 4,001,262, and are covered per se in the Hester, Jr., U.S. Pat. No. 3,987,052 or 3,734,922. They are referred to herein as the 'estazolam-type' compounds, because one of these 1-unsubstituted compounds, 8-chloro-6-phenyl-4H-s-triazolo[4,3-a][1,4]benzodiazepine, now has been named officially with the generic name, estazolam.

The products described in Gall U.S. Pat. No. 4,001,262, and the 1-[(dimethylamino)methyl]-4-hydrogen-6-substituted-4H-s-triazolo[4,3-a][1,4]benzodiazepine compound products claimed in Hester, Jr., U.S. Pat. No. 4,250,094 are the mainly intended products of the improved process of this invention.

There are at least two aspects of the improved process. In the first aspect, we have discovered that addition of an alkali metal carbonate, preferably potassium carbonate, and preferably in at least a molar equivalent amount, relative to the content of the dimethylamino methylene salt in the mixture, and relative to the 1-hydrogen starting material in the solvent, preferably containing at least a molar amount of N,N-dimethylformamide (referred to herein as DMF) or N,N-dimethylacetamide (DMAC) minimizes byproduct formation.

The added potassium carbonate, or equivalent alkali metal salt, appears to minimize double bond migration within the starting material structure (I), so as to minimize resultant-susceptibility of the molecule to form 4-aminomethyl structure (III) and thence the 1,4-bis-(aminomethyl) structure (IV) by-products, thereby enhancing the theoretical and practical yield probabilities of forming more of the desired 1-(dimethylamino)-methyl product (V).

We prefer to conduct this reaction between the 1-hydrogen-6-substituted-4H-s-triazolo[4,3-a][1,4]benzodiazepine and the dimethylaminomethylene salt in the presence of the alkali metal carbonate in a solvent such as DMF or DMAC at temperatures of about 20° C. to about 60° C. preferably 47° to 60°, for about 2.5 to 16 hours. The lower temperature range than those suggested by the above Gall U.S. Pat. No. 4,001,262 helps minimize by-product formation.

The second aspect of the improved process of this invention has to do with treatment of the 1-[(dimethylamino)methyl]-6-substituted-4H-s-triazolo[4,3-a][1,4]benzodiazepine product containing reaction mixture. When the reaction between the starting material (I) and the dimethylaminomethylene salt is complete as desired, the reaction mixture is cooled to room temperature or below, quenched in a cold aqueous-acid solution and the resulting mixture is adjusted to a pH between 3.0 and 4.0 and then extracted with a halogenated $C_1$ to $C_2$-alkane liquid solvent such as methylene chloride, methylene bromide, chloroform, tetrachloroethane, and the like, but preferably with methylene chloride, one or more times. The halogenated alkane liquid phase, containing the 1-[(dimethylamino)methyl]-6-substituted-4H-s-triazolo[4,3-a][1,4]benzodiazepine product (V), can be then separated from the aqueous phase, treated with aqueous basic solution and dried over a drying salt such as sodium sulfate or magnesium sulfate, filtered, and concentrated to low volume to remove the halogenated alkane solvent and to leave as residue an oil containing the crystalline product (V) which crystalline product can be filtered and dried to constant weight by vacuum oven drying overnight at about 40°-55° C.

We have discovered that for this process to be reasonably effective in separating any undesired by-products (III) and (IV) and the by-product salts it is necessary to adjust the pH of the DMF/aqueous product (V) containing mixture to between pH 3.0 and 4.0 before extracting the product (V) into the methylene chloride or other halogenated alkane extracting liquid. We have found that attempting to conduct this extraction when the pH of the mixture is too much above pH 4.0, say at pH 5.0-5.5, there are obtained in the methylene chloride extracts unacceptably high contaminating amounts of by-products (III) and (IV). At pH much below 3.0, the desired product is protonated and remains in the aqueous layer. Conducting the extraction too much below pH 3.0, say at pH 2.0, is prohibitively inefficient. Some of the DMF or other solvent may be carried over into the methylene chloride or other extracting liquid with the product (V), but the DMF can be removed from the separated methylene chloride solution of the product (V) by washing the solution with a basic water wash, adjusted to pH 8.0 to 14.0, preferably to pH 8.5 to 9.0, e.g., with sodium bicarbonate solution or with sodium hydroxide solution which basic, aqueous washes can be used one or more times, say up to 5 times to remove essentially all of the reaction mixture solvent, e.g., the DMF or DMAC, from the product of the process (V).

It is known that under acidic conditions triazolobenzodiazepine compounds are in equilibrium with the corresponding ring opened triazolylbenzophenone compound: see N. Inatsume, et al. Chem. Pharm. Bull Japan, Volume 28 (8), pages 2536–2540 (1980). Because of this fact, the above final wash to remove the reaction solvent is done with a basic aqueous solution to close any ring opened compound which may be present.

Examples of compound products (V) which can be prepared by the process inprovement of this invention are named, for example, in Gall, U.S. Pat. No. 4,001,262 and Hester, Jr., U.S. Pat. No. 4,250,094, which patents are incorporated herein by reference.

The invention is further illustrated by the following detailed examples which are not intended to be limiting, but which do illustrate the process improvements of this invention applied to the production of adinazolam (a structure V compound) from estazolam (a structure I compound) starting material. As a class, the products V of the process of this invention are known to have useful ranges of Central Nervous System (CNS) properties making them useful in appropriate dosage amounts and pharmaceutical forms as one or more of anti-anxiety, tranquilizer anti-depressant or anti-psychotic drug compounds. Thus, the detailed examples here are applied to the laboratory scale and pilot plant scale production of adinazolam to illustrate the operability of the process improvements claimed herein.

EXAMPLE 1

Laboratory Scale

The reagent, dimethylmethylene ammonium chloride, (see Gall, U.S. Pat. No. 4,001,262, Example 1, column 3, lines 31 to 37) was prepared here by mixing a solution of 1.53 g (15 mmoles) of bis(dimethylamino)methane in 40 ml of DMF at 0° C. with 1.178 g (15 mmoles) of fresh, commercially available acetyl chloride in 2.0 ml of DMF. This salt solution was treated with 2.48 g (18.0 mmoles) of solid potassium carbonate. This mixture was stirred for 5 minutes and then a solution of 2.947 g (10.0 mmoles) of estazolam in 15.0 ml of DMF was added. The resulting mixture was heated to 60° C. for a total heating time of 3 hours, after taking small aliquot samples of the reaction mixture.

The resulting reaction mixture was quenched with a cold solution of Buffar 401 (a commercial buffer (pH 4.01) from Mallinckrodt). The resulting buffered mixture was treated with 60 ml of 2 percent hydrochloric acid in water solution to adjust the pH of the mixture to 3.5. The acidified mixture was extracted five times with 200 ml portions of methylene chloride. The methylene chloride extracts were combined, washed with 10 percent w/v sodium hydroxide in water solution, separated from the resulting aqueous layers, dried with sodium sulfate, and concentrated in vacuo to leave as residue 2.75 g of oil, which was taken up in ethyl acetate and crystallized therefrom to give 1.303 g of adinazolam prism crystals (first crop) for a 37.1 percent yield. The melting point of this crude crystalline adinazolam was 167.5°–169° C.

The above aqueous layer was re-extracted (at pH 3.5–4.0) with methylene chloride (4×200 ml portions), which extracts were combined, washed as above, dried and concentrated to obtain 0.444 g of oil (crude adinazolam product). This oil was combined with the above crude crystalline adinazolam mother liquor, which mixture was taken up in ethyl acetate and the product, adinazolam, was crystallized therefrom, to give an additional 0.470 g of prism crystal adinazolam, m.p. 167.5°–169° C., for an additional 13.4% yield.

The aqueous layers were again re-extracted with six 200 ml portions of methylene chloride, at pH 4.0, the extracts were combined, washed, dried, extracted with sodium hydroxide aqueous solution, as above, to remove any hydrogen chloride, dried and concentrated to obtain crystalline product adinazolam, 390 mg., m.p. 166°–167° C., for an additional 11.11% yield. The total yield was 61.6% adinazolam.

EXAMPLE 2

Pilot Scale

The space in a 300 gallon glass reactor pair is evacuated and flushed three times with nitrogen to remove air and to render the space therein inert. Using a vacuum device there is drawn into the glass lined reactor from grounded containers, 10.382 kg of N,N,N',N-'-tetramethyldiaminomethane and 50 liters of essentially anhydrous N,N-dimethylformamide (DMF) (e.g., Karl Fisher water test analysis≅0.003). The reactor is cooled to between −25° and −30° C. by circulating a brine (chilled methanol) solution through the reactor jacket.

In a second vessel, rendered inert by evacuating and passing nitrogen therethrough three times, there is added 14.3 kg of benzoyl chloride from a grounded drum.

Using polyethylene tubing and nitrogen pressure, the benzoyl chloride from the second vessel is slowly added to the solution in the glass lined 300 gallon vessel over about 3 hours keeping the temperature of the mixture below about −10° C. (Caution: this reaction is exothermic). After complete addition the mixture is stirred for 20 minutes to ensure complete reaction. Thereafter the brine cooling liquid is blown back out of the reactor cooling jacket.

Thereafter, with the process operator wearing a respirator, gloves and using a vent duct, the top (manhole) of the glass lined reactor vessel is opened and 15 kg of solid potassium carbonate is added. The vessel is closed, re-inerted with nitrogen and stirred for 20 minutes.

In a grounded bucket, there is slurried 20 kg of estazolam in about 40 liters of DMF. This resulting slurry/solution is transferred via a vacuum pump procedure to the above glass lined reactor, rinsing the bucket and transfer lines with 10 to 15 liters of DMF.

The resulting reaction mixture in the glass lined reactor vessel is heated, with stirring, to 40°–50° with warm water in the reactor jacket until samples of the reaction mixture indicate that the reaction is complete by thin layer chromatographic (TLC) procedures. This reaction is usually essentially complete in about 6 to 18 hours. At completion a TLC of a reaction mixture sample, using 10 percent methanol in ethyl acetate as eluting solvent, UV visualization, and a doubly eluted plate shows an Rf of the product of about 0.45, compared to an Rf of 0.5 for the starting material.

A separate glass lined reactor vessel is inerted by evacuating and flushing three times with nitrogen, and then 544 liters of distilled water is metered thereinto. To this water containing vessel the reaction mixture from the glass lined reactor is added with stirring, followed by addition of 10–20 liters DMF used to rinse the reactor and the transfer lines.

To a clean, dry separate vessel on the side, there is added 25 liters of concentrated hydrochloric acid from a grounded container, and this acid solution is added to the above water/reaction mixture, via vacuum and polyethylene tubing lines. This acid addition operation is repeated, for a total addition of 50 liters of concentrated hydrochloric acid solution. This adjusts the pH of the mixture to about pH 1. (This pH 1 step is optional but it is done here to facilitate removal of the neutral benzamide by-product formed from reaction of the diamine and benzoyl chloride.)

To the above water/reaction mixture/hydrochloric acid mixture there is added, from a grounded drum, 270 liters of ethyl acetate, the resulting mixture is stirred to a uniform consistency and then allowed to settle. The pH of the aqueous phase is checked and adjusted to pH 1.0, if necessary. This stir/settle/pH check operation is repeated two more times, to remove as much as possible of a reaction by-product from the aqueous/DMF liquid phase. The ethyl acetate/by-product phase containing some DMF is removed in this way from the product containing aqueous/DMF liquid phase.

The pH of the product containing aqueous/DMF phase is adjusted by addition of 50 percent w/v sodium hydroxide in water solution, to about pH 3.4, using a pH meter, while the operator wears protective equipment.

To the pH adjusted aqueous phase there is added 270 liters of methylene chloride via a solvent line, stirring and maintaining the pH at 3.4 by addition of small amounts of 50 percent sodium hydroxide aqueous solution. The extraction procedure is repeated, two or more times, to ensure transfer of as much as possible of the product to the methylene chloride liquid phase.

When essentially no more product remains in the aqueous liquid phase, the acidic aqueous phase of the mixture is treated with sodium bicarbonate to adjust the pH of the mixture to between pH 8.5 to about pH 9.0, preferably to about pH 8.9, and disposed of to a deep well.

The combined methylene chloride product containing phases are then treated with about 200 liters of water, the pH of the aqueous phase is adjusted to about 5.8 to 9.0 with 50 percent w/v sodium hydroxide in water solution, the mixture is stirred and the liquid phases are separated. This removes the bulk of the DMF from the organic phase. This aqueous basic wash procedure is repeated 5 times to ensure removal of essentially all of the DMF from the product in the methylene chloride phase. This basic water wash also serves to close up any ring opened material in the methylene chloride product containing phase while minimizing the amount of product that is extracted into the aqueous phase.

The organic, methylene chloride liquid phase is separated from the basic aqueous wash liquids and dried by filtration through sodium sulfate into a clean, dry vessel, and concentrated at 45° C. under jet vacuum to a small volume. The crystalline product, adinazolam, which forms is filtered and dried in a vacuum oven at 40° overnight. This adinazolam is then ready for further processing into pharmaceutical formulation dosage unit forms or into any desired pharmaceutically acceptable salt of adinazolam free base, which salt is then processed into pharmaceutical formulation dosage unit forms.

In the first above run the yield of adinazolam was 51.5%. In the second run the yield of adinazolam was 80.7%, based on the estazolam starting material when the scale of process was increased. The purity of the adinazolam product was about 99% by high pressure liquid chromatography (HPLC) analysis methods.

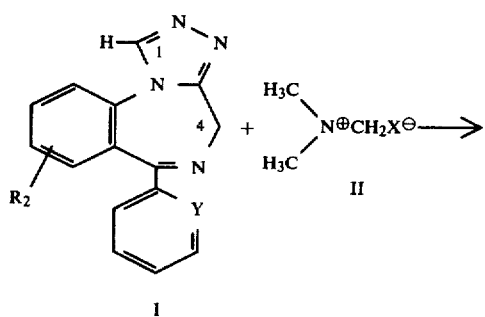

I

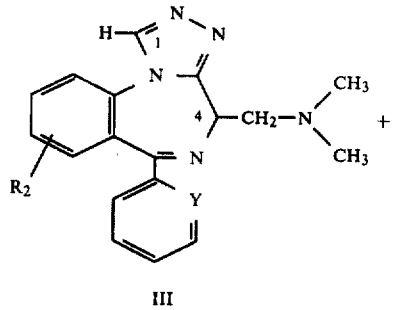

III

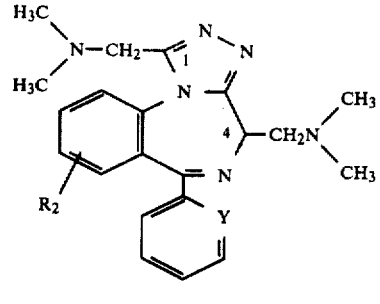

IV

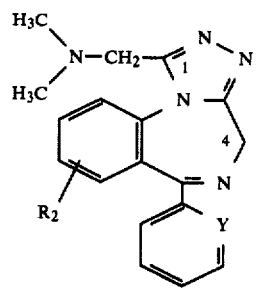

V

What is claimed is:
1. In a process for preparing 1-[(dimethylamino)methyl]-6-substituted-4H-s-triazolo[4,3-a][1,4]benzodiazepine (V) by reacting a 4H-s-triazolo[4,3-a][1,4]benzodiazepine (I) with the reagent

(II)

where X⁻ signifies the anion of an acid, in an organic liquid solvent, the improvement which comprises conducting the reaction between the 1-unsubstituted-6-substituted-4H-s-triazolo[4,3-a][1,4]benzodiazepine (I) with the salt

(II)

reagent (II), in the solvent, in the presence of an alkali metal carbonate salt, at a temperature of from about 20° to 60° C. for a time sufficient to form the product 1-

[(dimethylamino)methyl]-6-substituted-4H-s-triazolo[4,3-a][1,4]benzodiazepine (V).

2. A process according to claim 1 wherein the alkali metal carbonate is potassium carbonate.

3. A process according to claim 1 which further includes the steps of mixing the resulting product (V) containing organic reaction mixture with water, and adjusting the pH of the aqueous phase of the resulting mixture to between pH 3.0 and pH 4.0;

extracting the product (V) from the resulting pH adjusted mixture into a $C_1$ to $C_2$ chlorinated, saturated hydrocarbon organic liquid solvent therefor, separating the organic and aqueous liquid phases, treating the organic halogenated hydrocarbon liquid product (V) containing phase with a pH 8.5 to pH 14 aqueous basic wash to remove any remaining reaction mixture solvent, and to force closure of any ring opened product, separating the resulting aqueous and organic halogenated hydrocarbon liquid phases, and recovering the product (V) from the resulting organic liquid phase containing the product.

4. An improved process according to claim 1 for preparing adinazolam which comprises contacting and reacting estazolam with a dimethylaminomethylene salt in N,N-dimethylformamide or N,N-dimethylacetamide in the presence of potassium carbonate at 47° to 60° C. for a time sufficient to form adinazolam in said reaction mixture.

5. A process according to claim 4 which further includes the steps of mixing the resulting reaction mixture with water and acid in amounts to adjust the pH of the mixture to about pH 1, extracting the acidified mixture with ethyl acetate, adjusting the pH of acidified aqueous, product containing liquid phase to between pH 3.0 and 4.0, extracting the pH adjusted aqueous phase with methylene chloride to take up therein the product adinazolam, treating the methylene chloride product containing phase with a pH 8.5 to pH 9.0 aqueous basic wash to remove any remaining reaction mixture solvent, and to force closure of any ring opened product, separating the aqueous phase from the methylene chloride liquid phase, and recovering adinazolam from the methylene chloride liquid phase.

* * * * *